United States Patent [19]

Rushbrooke et al.

[11] Patent Number: 4,922,092

[45] Date of Patent: May 1, 1990

[54] HIGH SENSITIVITY OPTICAL IMAGING APPARATUS

[75] Inventors: John Rushbrooke, Girton; Adrian Lyons; Patricia Tomkins, both of Turnbridge Wells; Richard Ansorge, Cambridge, all of England

[73] Assignee: Image Research Limited, England

[21] Appl. No.: 216,713

[22] PCT Filed: Nov. 20, 1987

[86] PCT No.: PCT/GB87/00824

§ 371 Date: Jul. 7, 1988

§ 102(e) Date: Jul. 7, 1988

[87] PCT Pub. No.: WO88/04045

PCT Pub. Date: Jun. 2, 1988

[30] Foreign Application Priority Data

Nov. 26, 1986 [GB] United Kingdom ............... 8628285
Oct. 4, 1987 [GB] United Kingdom ............... 8708615

[51] Int. Cl.⁵ .......................................... H01J 31/50
[52] U.S. Cl. ........................... 250/213 VT; 250/361 C
[58] Field of Search ......... 250/213 R, 213 VT, 361 C

[56] References Cited

U.S. PATENT DOCUMENTS 3,963,928  6/1976  Zolner .......................... 250/361 C
4,555,731 11/1985  Zinchuk ....................... 250/213 VT
4,704,522 11/1987  Hirai et al. .................... 250/213 VT Primary Examiner—David C. Nelms
Attorney, Agent, or Firm—Lee, Mann, Smith, McWilliams & Sweeney

[57] ABSTRACT

Apparatus wherein an image intensifier (16) is interposed between a plurality of emission sites (10) from which emanate photons and a photo-detector (20) coupled to the output of the image intensifier to produce separate electrical signals processed by computer (24) to enable the respective signals to be correlated to the sites of the original emission source.

27 Claims, 7 Drawing Sheets

4,922,092

HIGH SENSITIVITY OPTICAL IMAGING APPARATUS

FIELD OF INVENTION

This invention concerns high sensitivity optical imaging apparatus, more especially for low light level detection particularly in the field of bio-medicine for the detection and measurement of very small quantities of light emitted by diagnostic samples treated with suitable reagents. By way of example, blood serum or other body fluids when mixed with certain reagents derived from monoclonal antibodies, produce photonic emission in the presence of certain antibodies or the like. The principle applies generally to tissue sections and electrophoretic gels and the like.

BACKGROUND TO INVENTION

The detection of low level photonic emission from chemical reactions in the field of bio-chemistry has become of increasing importance as techniques have been developed which involve the mixing of one or more reagents with blood serum or other body fluids to determine whether or not and to what extent antibodies or antigens or the like are present in the body fluid, depending on whether or not and how much photonic emission occurs following the mixing of the reagents with the body fluids. These techniques have been developed for mass screening of diseases such as certain cancers and latterly AIDS.

In such techniques, liquid samples to be tested are placed in each of the wells in an opaque tray typically formed from plastics material. A typical tray will comprise 96 such wells each of 6 mm diameter on a 9 mm spacing. The 96 wells form a 12×8 array. Each well enables a single test to be carried out with a particular reagent-sample combination. Thus the 96 wells together enable up to 96 tests to be carried out simultaneously with many possible combinations of different tests for one individual or the same test for different individuals.

The main problem associated with photonic emission diagnostic techniques is the very low rate of photon emission associated with most such reactions. The signal-to-noise ratio of most conventional electronic photo detectors is far too low to enable such low photonic emission to be detected and attempts have been made to improve the sensitivity of conventional photon detectors as by cryogenic cooling techniques to reduce the electrical activity of the detector, (and hence the noise), to an acceptable level, and thereby enable the detector to respond to very low photon emission rates.

However such devices still do not possess the level of sensitivity which is desirable since the coupling efficiency between the light output from the individual wells and the photon detector has tended to be very poor. Additionally the charge coupled devices normally used as such detectors tend to have a very low efficiency (typically of the order of 30%) at the wave length (typically 420 nanometers) associated with luminescent assay measurement.

The use of wavelength conversion layers to achieve higher efficiency has significant associated problems.

Other proposals have utilised imaging photon detectors the output of which comprises digital signals corresponding to the X,Y co-ordinates at which a photon event has been detected. However such devices operate on a random sampling basis and tend to saturate and become insensitive to low light level sources in the presence of high light level sources. Such devices therefore do not lend themselves to general use for testing sample trays where there can be considerable disparity between the photon emission from one well and from another.

Known proposals are also disadvantageous in other fields demanding low level light detection, such as gel electrophoresis.

It is therefore one object to the present invention to provide apparatus including an improved photon emission detector capable of a wide dynamic range and yet capable of responding to and producing an output signal in the presence of very low rates of photon emission.

It is further object of the invention to provide a luminescent assay measuring system capable of responding to very low photon emission rates for use in the detection of virus infections and cancerous cells, particularly in tissue sections as found in histology.

Moreover, in the microscopic examination of a sample on a microscope sample-holder, even at low magnification the operator sees only a small part of the sample at any one time, and is required to scan the entire sample to find any one or more sites of particular interest, which can then be examined in more detail at high magnification. Operator scanning of the entire sample in this way is time consuming and expensive, and therefore a further object of the present invention is to provide an image quantifier which assists in the solution of this problem.

However, the imaging apparatus of this invention is of general applicability in the fields of fluorescence microscopy, luminescence microscopy, interferometry, spectroscopy, X-ray digital imaging, and gel electrophoresis, for example, as well as in related fields of endeavour where high sensitivity optical imaging is required.

SUMMARY OF THE INVENTION

According to the present invention, there is provided high sensitivity optical imaging apparatus comprising an image intensifier adapted to be optically coupled to a sample holder to receive on distinct regions of its input faceplate photon emission emanating from differing sites on the sample holder carrying one or more samples, photoelectric detecting means coupled to the output of the image intensifier to produce electric output signals dependent on the photon emission received at the respective distinct regions of the faceplate, and signal processing means for relating the respective output signals to the originating sites of photon emission by the sample or samples carried by the sample holder.

As examples of the invention the following will be considered namely (a) an image quantifier by which a sample can be viewed by an image intensifier and a microscope, (b) a photon detector for measuring light emission from a plurality of discrete reaction sites, and (c) apparatus for measuring a number of columns of line sources of radiation, as in gel electrophoresis.

In the first mentioned example, an image quantifier includes a sample holder which permits the contained sample to be viewed by an image intensifier and a microscope.

Thus in accordance with this aspect of the invention there is provided an image quanitifer in which the sample holder has an underside for directly supporting the sample which is made from optic fibre glass, and there is provided an image intensifier having a fibre optic faceplate optically coupled to the underside of the sample holder to receive light, unit area by unit area, from the entire area of the sample, a CCD sensor having at least one photosite (pixel) for each unit area of the sample, said CCD sensor being optically coupled to the output face of the image intensifier, electronic means for cyclically reading the image accumulated on the CCD, means for processing the resulting electrical signals, and a means drivable by the processed signals to enable an operator to identify any site of interest in the sample.

Means may be provided to control the illumination of the sample whilst viewing by the image intensifier to thereby prevent saturation of the intensifier.

When employed to view self luminescent samples, all other external light sources can be excluded.

When high light levels are required for conventional microscopic viewing of the sample the image intensifier high voltage supply may be automatically cut off or a shutter might be used to cut out light.

The signal processing means preferably comprises means for digitising the signals obtained from the CCD and means for storing the digitised signals. The stored signals may be read out to drive a display device in any of a variety of ways, utilising computer graphics. In addition to displaying a two-dimensional view of the entire sample, for example, the stored signals may be utilised to enable a display device to show histograms of sections of the sample.

The stored signals may also be read out for the purpose of controlling a microscopic centering device, whereby a microscope is automatically centred on a site of interest in the sample.

When it is preferred to have operator selection of possible sites of interest, a display device, driven by the processed signals, can display some or all of the entire sample, to enable the operator to identify the coordinates of a site of interest and immediately move the microscope manually or otherwise to centre on that site and view it under high power, without any requirement for low power scanning of the entire sample with the microscope in order to select the site.

A fibre optic coupler may be employed to couple the output face of the image intensifier to the CCD.

In one practical arrangement, the image intensifier is capable of resolving the area to be examined into a large number of unit areas of the order of 50×50 microns, whilst the CCD has pixels with an area of the order of 22×22 microns, so that light from any one unit area of the sample is on average spread over about 4 to 5 pixels of the CCD.

The CCD may have a light receptive area less than the image intensifier, in which case a demagnifying fibre optic taper may be employed to couple the image intensifier to the CCD.

An option available may be to substitute a 1:1 fibre optic coupler, so that overall resolution is increased to allow unit areas of about 30×30 microns to be detected and displayed and checked in sequence, although the facility for viewing an image of the entire sample is thereby lost.

In one embodiment this substitution may be optional the normal demagnifying image coupler or the 1:1 coupler being selected as required.

The image accumulated on the CCD is preferably read out at TV frame rates using CCIR standards. However, the sampling period may be increased, for example up to 1 sec, if the signal obtained at TV frame rate has an insufficient signal to noise ratio.

The apparatus in accordance with the invention is capable of detecting and counting single photons emitted from any unit area of the sample, with a probability of detection dependent on the effective transparency of the fibre optic sample holder and the efficiency of the photocathode of the image intensifier. With an image intensifier with a photon gain of the order of $10^{-4}$, an optical taper efficiency of about 20%, and a CCD efficiency of about 30%, then about 8000 electrons are produced if a photon is detected. By comparison, CCD pixel noise at TV frame rate and at room temperature is about 200 electrons and, as light due to a single photon is spread over about 4 pixels, the overall noise level is less than 1/10th of the signal arising due to a single photon. The signal to noise ratio may be further improved if the CCD is cooled.

Saturation may occur if light emission is as high as $10^{+6}$ photons per second per unit area of the saple. At this level the signal to noise ratio is of the order of 600.

The sample holder may comprise a fibre optic bottom plate having a shallow well enabling the examination of liquid samples, the sample holder also having an upper glass plate located against the lower plate by means of a positioning ring to ensure efficient contact between the sample and the said lower plate. The two plates are then clamped together and may be located for observation by a microscope from above, and detection and measurement by the image quantifier from below.

Example (b) is normally associated with a photon detector capable of responding to very low rates of photon emission and typically comprise an image intensifier adapted to be positioned so as to receive on discreet regions of its input faceplate photon emission from each of a plurality of reaction sites, a photo electric sensor coupled to the output of the image intensifier to produce an electrical output current as a signal dependent on the photon emission received at the input of the image intensifier, from each of the reaction sites associated therewith; and circuit means for storing the electrical output currents as separate output signals in a manner which enables the separate output signals to be related to the originating reaction sites, the output signals thereby obtainable from the device corresponding to the photon emission, if any, detected from each of the individual reaction sites.

Each of the reaction sites may be coupled separately to the input faceplate of the image intensifier by light guide means adapted to couple each site with a discreet region of the input faceplate of the image intensifier. If desired the cross-section of each light guide may taper a little from the input end to the faceplate end so as to occupy a smaller area on the faceplate.

Such light guide means is particularly appropriate where the input face plate of the image intensifier is smaller in area than the overall area of the sample holder, such as a tray containing reaction wells.

Thus the light guides reduce in cross-sectional area as between the input ends associated with the sample holder (tray) and the output ends associated with the input faceplate of the image intensifier.

It is of course important that the photon emission from each cell is kept entirely separate from the photon emission from adjoining cells and to this end the light guides may be coated or otherwise covered with an opaque material which may to advantage present a light reflecting inwardly facing surface, to increase internal reflection within the light guide. Alternatively the light guides may be clad with transparent material of lower refractive index to transport more effciently the light in the manner of an optical fibre.

Preferably the tray containing the wells is covered with a transparent film typically of plastic material to isolate the cells one from the other and also from the remainder of the apparatus.

Typically a perforated opaque gasket is located between a light guide array and the covered tray to optically isolate each well, and its associated light guide, from its neighbors. The gasket may for example be formed from sponge rubber.

The photo electric detector or sensor is typically a charge coupled device such as the TH7852 as produced by Thomson. Such devices present an array of active sensors (or pixels) and in the device mentioned the array can be thought of as a rectilinear matrix of 144 rows with 208 pixels in each row.

The image intensifier is typically a multi stage demagnifying high gain image intensifier. Typically the device has an input faceplate diameter of 80 mm but an output diameter of only 7 mm.

The function of such an intensifier is to increase the number of photons available in the output in response to the arrival of photons at the input. The demagnification is preferably selected so as to reduce the overall size of the array of light sources at the input of the intensifier to the size of the light sensitive area of the photo electric detector or sensor. Thus a demagnifying image intensifier would be selected having an output diameter corresponding to the input diameter of the photo electric detector.

A charge coupled device can be operated in a manner to integrate photons received during a period of time and give an electrical output signal corresponding to the photon emission received by the detector at its input. Each individual pixel may be considered as a separate detector, or more preferably groups of pixels may be considered to form a plurality of separate detectors over the surface of the array, each group being made up of a number of adjoining pixels.

Each pixel in each such group can be addressed individually, or each group of pixels can be addressed as a whole, and an output signal produced by combining the output signals from each individual pixel in the group. Combination may be achieved as by averaging or summation.

The circuit means associated with a charge coupled device will permit a wide range of integration times to be used and it is envisaged that the test period during which photon emission is measured may be as short as a few milliseconds or as long as a few seconds.

Preferably the circuit means includes a signal integration means and is adapted to correct for pixel dependent black levels and perform flat field corrections during image readout, the total light coming from a single light source being obtained by summing of the contributions from the pixel or pixels in a group of pixels which is or are responsive to the light from the particular site.

Typically a flash Analogue to Digital Converter (FADC) may be incorporated so as to produce a digital signal value corresponding to the electrical charge associated with each pixel. Calibration tables can be maintained in random access memories and a pipeline strategy may be employed to permit the electronics to process sequentially each pixel in one readout cycle at rates currently up to ten million pixels per second.

Conventionally luminescent bio-chemical samples emit light in the blue part of the spectrum (of the order of 420 nanometers wavelength) where image intensifier photocathode efficiency is typically of the order of 20%. In combination with a typically 50% loss in transmission between individual cells and the image intensifier, this means an individual photon emitted by the reagent has a 10% chance of producing an output in the image intensifier.

If an image intensifier is utilised having a photon gain of 35,000, and a charge coupled device is used as the photo electric detector having a quantum efficiency of 25% for the photons emitted by the image intensifier phosphor, the number of signal electrons produced in the charge coupled device is approximately 3,500 per incident photon on average.

With a CCD pixel size of typically $30 \times 28$ microns and with approximately 120 pixels in each group associated with one of the photon sources in the reaction tray, this means an average of 30 signal electrons per incident photon in each of the 120 pixels in the group.

If desired the readout noise per pixel can be reduced to less than 25 electrons by Peltier cooling or the like.

In a preferred embodiment, if the detection probability is 10% the light produced (if any) from one photon (called case $n=1$) will be confined to some 20 of the possible 350 pixels, viewing each reaction site using a resolution of 15 line pairs per millimeter). The readout noise associated with the signal will be the square root of the number of pixels (i.e. the square root of 20) multiplied by the electron readout noise per pixel (i.e. 25), giving an approximate value of 112. This leads to a signal to noise ratio of 300 in the case ($n=1$), remembering that one detected photon produces 35,000 signal electrons.

In medical applications a false negative result is highly undesirable and it is therefore important to determine the probability that no photons are detected. It can be shown using Poisson statistics with a 10% detection probability that if ($n=46$), there is a probability of less than 1% that no photons will be detected. For ($n=69$) the probability is 0.1%. In this connection integration times of 1 second or more are possible for low rate measurements.

Where n is large, many photons will be detected and approximately the same quantity of light will enter each of the 120 pixels associated with each reaction site. On average each pixel will receive 30 electrons per detected photon. It is therefore necessary to consider the saturation characteristics of the charge coupled device and if saturation can be considered to occur at levels of 300,000 electrons per pixel, values of n up to about 10,000 electrons can be measured. However this limit is independent of integration time and if an integration time of a few milliseconds (typically 4 milliseconds) is used this would correspond to accurate measurement of a flux of 2.5 million incident photons per second.

To give the largest dynamic range both short and long integration times can be used while viewing a particular set of reaction sites. By using a photo electric detector such as type TH7852 which has good anti-blooming characteristics, electron signals from high flux sites will largely be prevented from spreading to associated regions of the charge coupled device which are viewing low flux sites.

If cross talk has to be further reduced, computer controlled shutters can be utilised to mask automatically high flux sites during a long integration cycle.

Using techniques such as this it is possible to achieve a dynamic range of the order of 54,000, (i.e. 2,500,000/46).

The invention has a distinct advantage over previous designs of low light level detector involving cryogenically cooled CCD arrays. Primarily this arises from the elimination of the need for a lens, and the incorporation of direct coupling between the light producing reaction sites and the input faceplate of an image intensifier, which increases the photon coupling between the sources and the intensifier, and enhances the number of photons available for supply to the detector. If a lens were to be used to capture the photon emission from a reaction site, and feed it directly to such an array, the actual photon capture can be typically 1300 times worse than the predicted value of 0.1 for the present invention. A direct imaging device which in accordance with this present invention, does not utilise direct coupling and an image intensifier could thus require very long integration times of the order of tens of minutes.

The present invention also resides in apparatus for multiple luminescent assay measurement, comprising an image intensifier; means for receiving and supporting a tray containing a plurality of regularly arranged reaction wells, so that light emitted from the wells is received by discreet regions of the faceplate of the image intensifier; a multi-element photo electric array detector adapted to receive light from the output of the image intensifier and to produce electrical output signals indicative of the light received from each cell during an integration period; and electrical circuit means for controlling the integration time and producing electrical output signals whose values correspond to the photon emission from the related wells in the tray.

In view of the enhanced sensitivity of a detector embodying the present invention, involving fast data reduction and total measurement times of less than 10 seconds for a tray of 96 samples, it is possible to consider monitoring time dependent aspects of the individual reactions, by way of multiple measurement sequences, which may comprise time-lapse repeats of the basic measurement which if undertaken at high speed (e.g. every few milliseconds) will allow rapid time decaying systems to be studied, and if repeated at greater intervals (e.g. after some minutes) will allow long term changes to be observed.

The invention also envisages the aluminating of the bottoms and/or walls of the wells in the tray to improve the light yield from each individual well.

As embodied in the third example (c), the invention can also be used for the measurement of thin sections either directly or via an intermediate fibre optic coupling. Thus instead of the example of a 96-well tray of independent photosites, a number (e.g. six) of columns of line sources of radiation, as in gel electrophoresis, can be sensed by using appropriately modified light guides. Thus, 200 shaped guides, of 1 mm diameter at the output end, and of $1 \times 10$ mm$^2$ rectangular area at the source end, where they are close packed to cover a column area of $200 \times 10$ mm$^2$, may be employed. Where visible photons emerge from the source, e.g. where a scintillator is incorporated in the source material, then these shaped guides can be of simple plastics or glass. Where the sample emission is X-ray, gamma-ray or charged particle, then the shaped ends themselves can be manufactured from a suitable scintillating material.

The invention may also be used to measure reactions occurring in micro flow cells.

The enhanced sensitivity not only enables very low photon emissions to be detected and measured in the first place, but also enable the simultaneous measurement of a large number of samples in a very short space of time which is a fundamental pre-requisite of any mass screening technique such as may be required for screening an entire population for a virus infection or the like.

Although reference has been to assay measurement of 420 nms it is to be understood that the present invention is not limited to this wavelength, but may be used for detecting visible or invisible (i.e. UV or IR) radiation of any wavelength. Furthermore, optical filters can be introduced between the reaction sites and the faceplate of the image intensifier to select a particular wavelength or wavelengths emitted by the reagents, should this prove advantageous or necessary.

The invention will now be described by way of example with reference to the accompanying drawings in which:

FIG. 4A shows an enlarged portion of a sample tray;

DETAILED DESCRIPTION OF DRAWINGS

Figure 1:
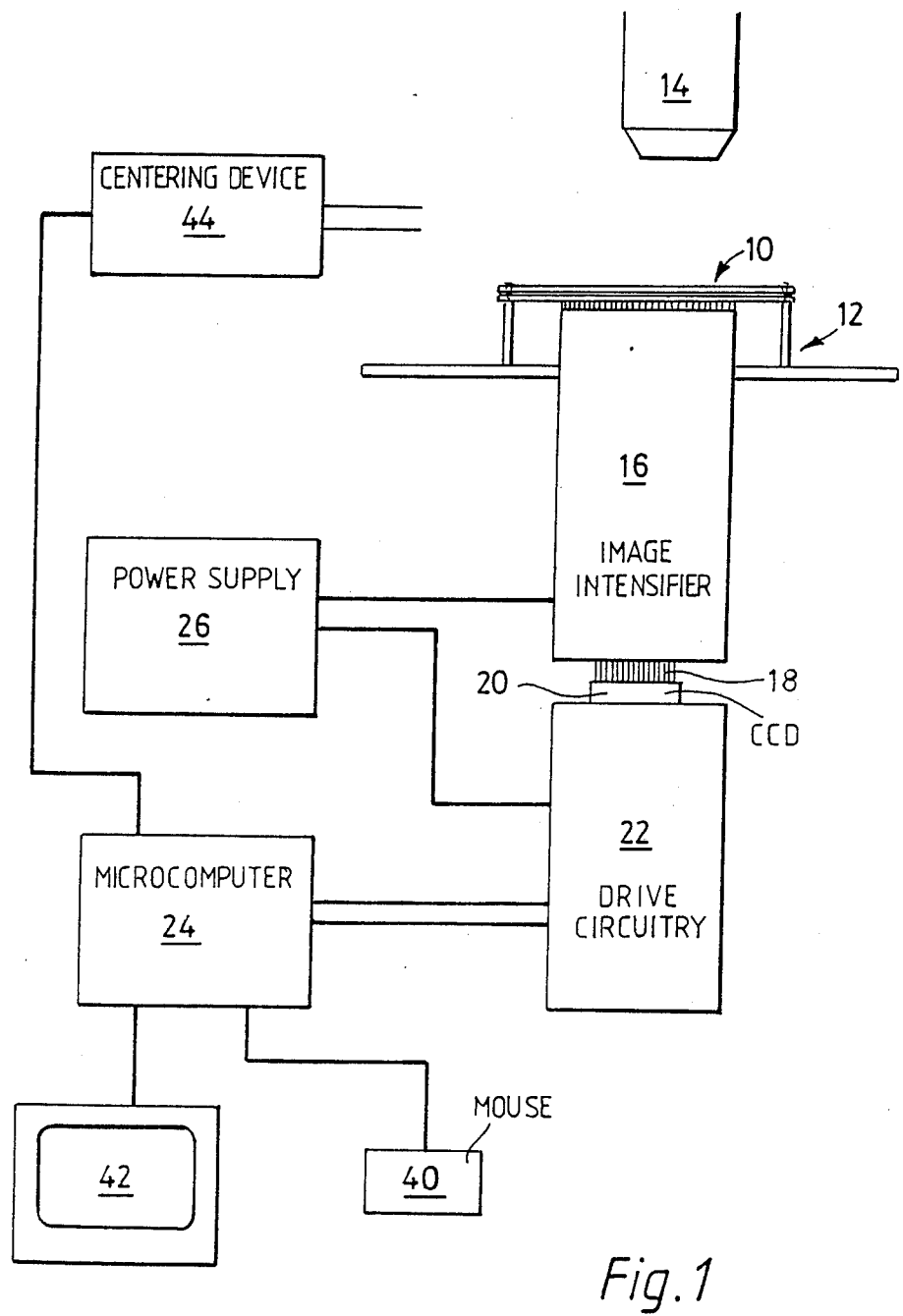
FIG. 1 is a schematic view of one embodiment of the complete apparatus.

Referring first to FIG. 1 (illustrative of example (a) hereinbefore mentioned), a sample holder 10 is carried by a support assembly 12 beneath a microscope 14. The image quantifier of this invention is positioned to view the sample from below, and comprises a high gain image intensifier 16, a fibre optic coupler 18 coupling the image intensifier output to a CCD 20, CCD drive circuitry 22 controlled by a microcomputer 24, and a controlled power supply 26. Output signals from the CCD are taken via processing circuitry to a display device 42 and possibly also to a microscope centering device 44. The processing circuitry (also not shown) conveniently includes a digitiser and a store, the accumulated image on the CCD 20 being read at TV frame rate.

Centering of a site in the field of view may be achieved as follows. The whole field is shown on the display device 42 by the control computer 24. A graphics pointer is simultaneously diaplayed and is moved by the operator using, for example, a mouse 40 to coincide with the chosen site. The computer then notes the position of te pointer and computes signals passed to an x-y stage control device 44 which then moves either the sample or the body of the microscope so as to centre the site of interest. Use of suitable image processing software would permit automatic centering without operator intervention where certain shapes are recognisable by the software.

A suitable image intensifier is an 18 mm diameter tube incorporating microchannel plate intensification, for example as manufactured and sold by Mullard. A suitable CCD is the GECP8600 or EEVP8602. These units may be coupled by an optical fibre taper having a de-magnification factor of about 1.7, or by a straight coupler as required by the application.

Figure 2:
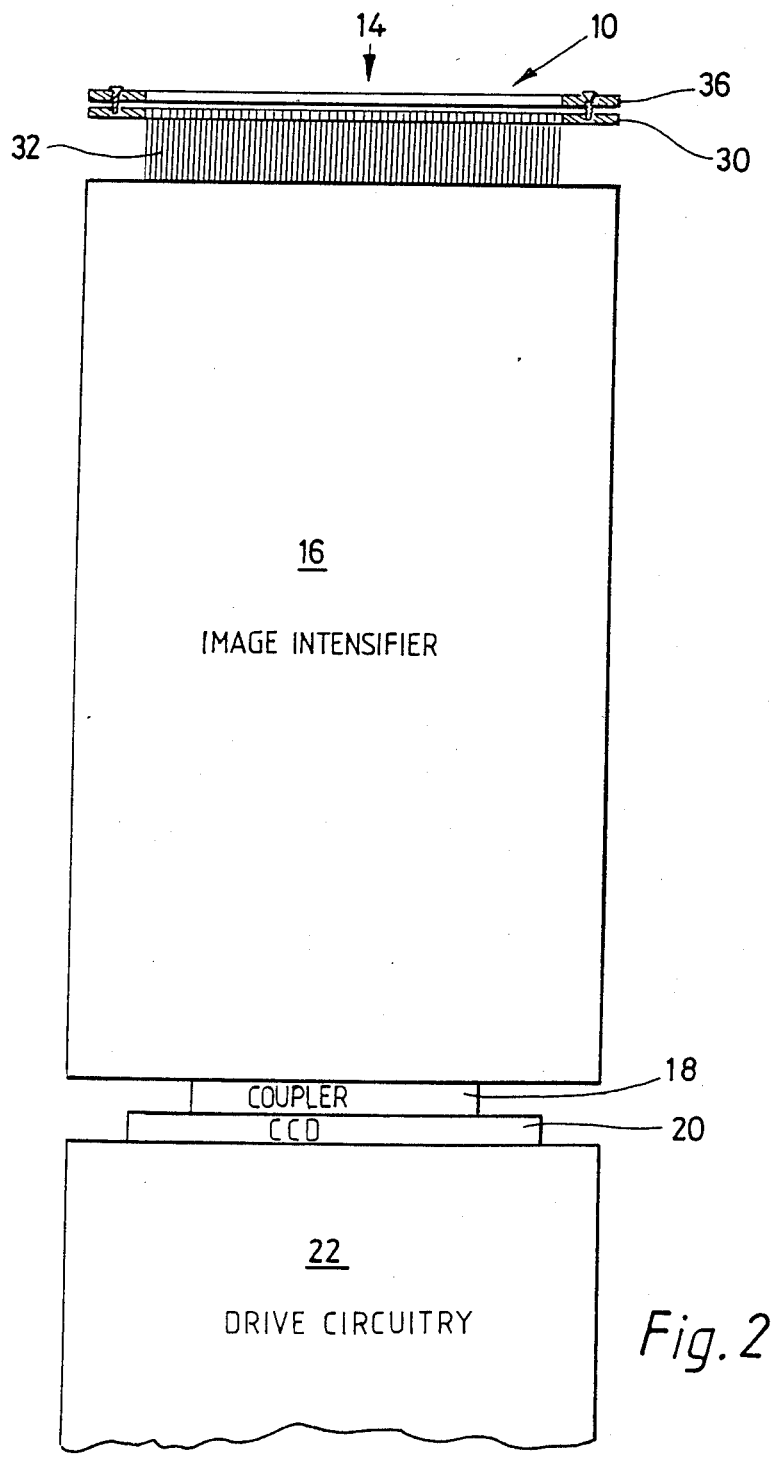
FIG. 2 shows part of the apparatus in more detail.
Figure 3:
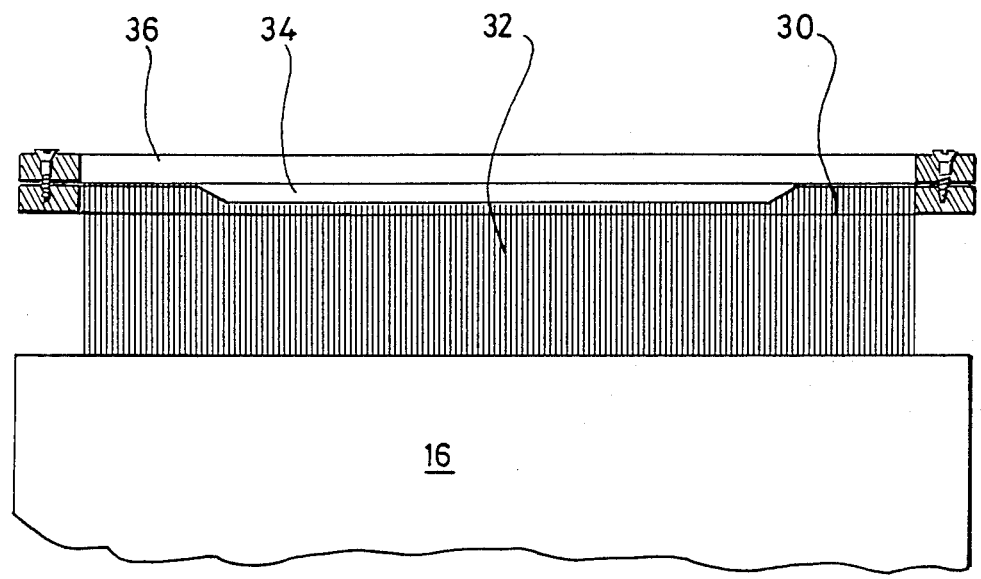
FIG. 3 shows a modified sample holder.

The sample holder 10 (see also FIGS. 2 and 3) comprises a bottom plate 30 of fibre optic glass, in direct contact with the fibre optic face plate 32 of the image intensifier 16. As shown on FIG. 3, this bottom plate 30 may be formed with a shallow well 34 for supporting liquid samples. An upper glass plate 36 clamps against the lower plate to ensure efficient contact of the sample with said lower plate. However, in the case of a well-shaped lower plate, it may be possible to dispense with the upper plate. Said fibre optic lower plate is important for preventing degradation of resolution in transferring the optical image into the image intensifier.

The illustrated apparatus is capable of optical imaging at very high resolution, i.e. down to unit areas of sample as small as 50×50 microns or even 30×30 microns, with a worst possible signal to noise ratio of about 10:1 even in the case of single photon detection.

Figure 4:
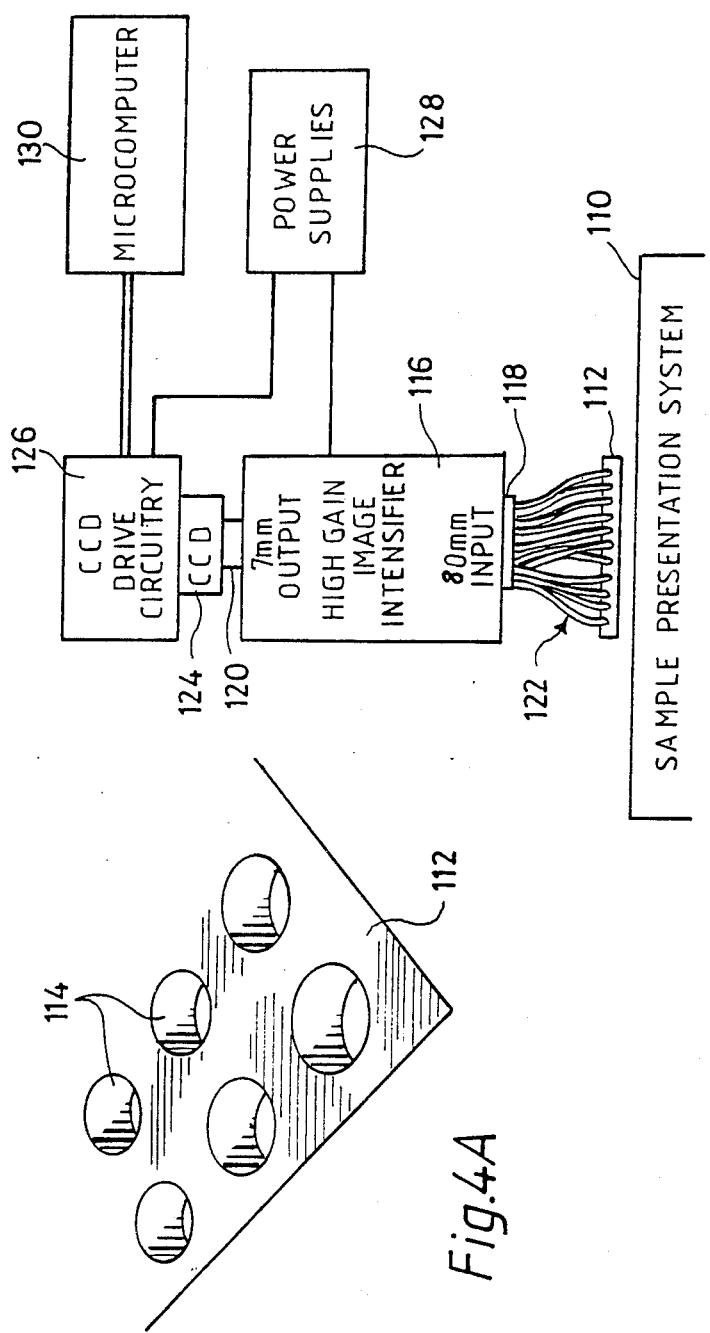
FIG. 4 is a block schematic diagram of a complete detector system embodying the invention.

Considering next example (b) hereinbefore mention, FIG. 4 shows a complete detector system comprising a support table 110 in which is mounted a sample tray 112 of the type formed from a thin sheet of plastic material shown in FIG. 4A in which the sheet material is deformed at regular intervals across the area of the sheet to form cylindrical wells 114 into which liquid samples can be deposited.

A typical tray has 12 rows with 8 wells in each row of wells.

Typically the spacing between the centres of adjoining wells is 9 mm and the diameter of each well is approximately 6 mm.

In use samples are deposited in the wells in the tray and a reagent material added to each sample. In the type of analysis envisaged, reagents are selected which when added to the sample fluids in the wells will produce a fluorescence or phosphorescence or other photonic emission, usually at very low levels, in the event that some organism or virus or antibody or other constituent is present in the sample fluid. Due to the very low light levels associated with such reactivity a very sensitive detector must be employed which is capable of receiving and integrating the photonic emission from each sample for a reasonable period of time in order to produce an output signal indicative of the reaction which has occurred. Thus if at the end of a test period of time, no significant photon emission has been detected, the fluid and the reagent material can be considered to be non-reacting, and vice versa.

In accordance with the invention, the very low light level emission is enhanced using an image intensifier 116. Typically a demagnifying image intensifier is used having an input faceplate 118 of typically 80 mm diameter and an output window 120 typically having a diameter of 7 mm. Typically the image intensifier is a high gain intensifier as well as being a demagnifying intensifier.

Between the individual wells in the sample tray 112 and the input faceplate 118 are provided a plurality of light-guides generally designated 122 which serve to couple the light output from each well to a discreet region of the input faceplate 118. Detail of the light guides 122 and the decoupling and cross talk reducing features of this part of the apparatus will be described in more detail in relation to later figures.

A charge coupled device (CCD) camera 124 is coupled in a light tight manner to the output window 120 of the image intensifier 116 and drive circuitry for the CCD camera is provided at 126.

Power supplies for the image intensifier and CCD camera are denoted by 128 and an output signal from the CCD drive circuitry 126 is shown being supplied to the input of a microcomputer 130 which is adapted to process the information and deliver an output information signal for each of the wells in the original sample tray.

Figure 5:
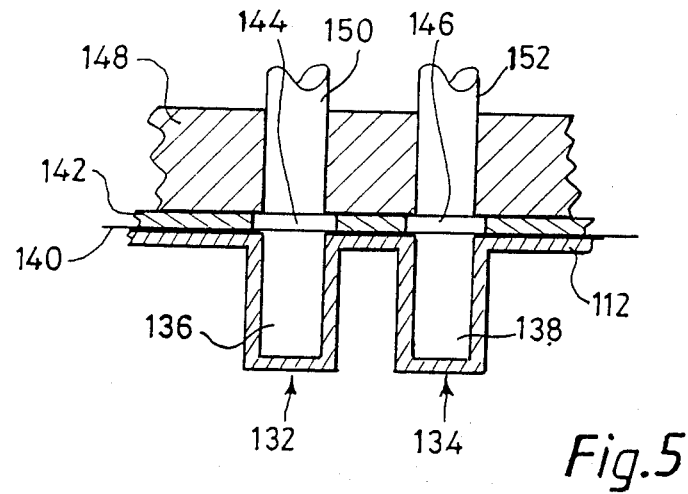
FIG. 5 is a side view to an enlarged scale of the interface between the lower ends of the light guides and the wells in the sample tray.

FIG. 5 illustrates in cross-section part of the sample tray 112. Two wells 132 and 134 are shown in FIG. 5 each containing a liquid sample 136 and 138 respectively.

A thin transparent plastic membrane 140 is stretched over the top of the tray to prevent any accidental mixing of the samples should the tray be shaken and to reduce the possibility of infection or contamination whilst the tray is being handled. Typically the membrane 140 is of so called cling-film material.

Above the membrane 140 is located a compressible rubber gasket 142 which includes a pattern of apertures, two of which are shown at 144 and 146, which align with the wells in the tray. Thus apertures 144 and 146 align with wells 132 and 134. The rubber is compressible and may for example be a sponge rubber material. It is however important that the material is opaque to light and acts as a complete barrier to the lateral transmission of light emanating from the surface of the liquid samples such as 136 and 138.

Above the gasket 142 is located an opaque support plate 148 having a plurality of apertures which correspond in number and position to the number and position of the wells and through which transparent light guides can pass and in which the said light guides are secured. In FIG. 5, two such light guides 150 and 152 are shown passing through the plate 148 to form transparent windows in the underside of the plate 148 in alignment with the wells 132 and 134.

The material from which the tray 112 is manufactured is itself opaque to light or if not is coated on either one or both surfaces with an opaque material such as a paint.

An improvement can be obtained by silvering or otherwise rendering reflective the inside walls of the cells 132 and 134.

Where a transparent material is used for the tray material, the external surface of the tray may be silvered instead of the inside surface and the silvering may serve the dual purpose of reflecting light from the sample towards the light guide related there to and which would other wise be lost and in addition render the otherwise clear plastic material opaque.

Although the term "silvering" has been employed, it is to be understood that this is not limited to the type of material used to produce the reflective surface and an aluminium coating or foil may be employed to produce the reflective surface, as may other materials.

Figure 6:
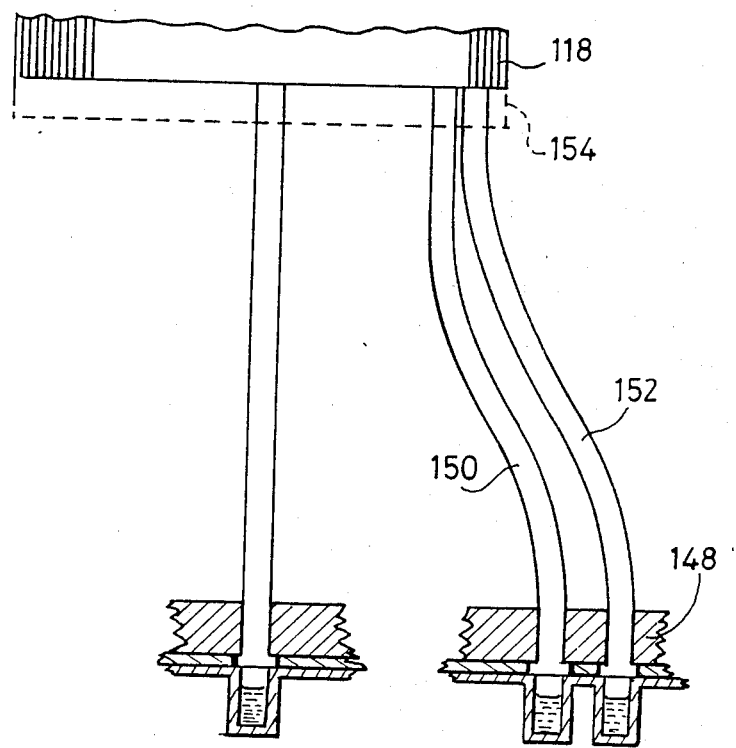
FIG. 6 is a further side view also to an enlarged scale showing the manner of coupling between the individual wells and the face plate of an image intensifier.

FIG. 6 demonstrates how the light guides map from the plate 148 to the input faceplate 118 of the high gain image intensifier 116 of FIG. 4. Generally the wells will be arranged in a rectilinear array whilst the faceplate of the image intensifier 118 will be generally circular and the diameter of the faceplate will probably be somewhat smaller than at least the longer dimension of the rectinilear array of wells. Provided the cumulative area of cross-section of the light guides and of the spaces between them on the faceplate is no greater than the area of the faceplate 118, and provided the light guides can be bent as shown in FIG. 6 and if necessary tapered to achieve this, all of the individual light guides such as 150 and 152 can be mapped between the rectilinear array in the plate 148 into a generally circular array to cover the faceplate 118. A second opaque plate shown in dotted outline at 154 may be provided to reduce unwanted light input and cross talk at the intensifier input and for mechanical support.

Figure 7:
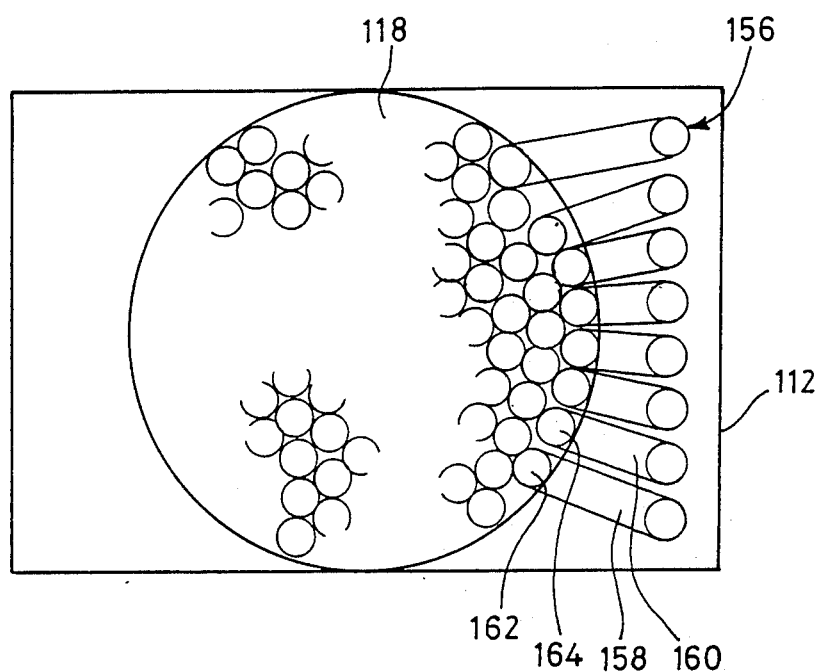
FIG. 7 illustrates the possible mapping of one 8-well column onto part of a circular intensifier faceplate to scale.

FIG. 7 illustrates the mapping from the generally rectangular tray 112 to the circular input faceplate of the image intensifier 118, as viewed along the axis of image intensifier. Thus a right hand column of wells generally designated 156 is shown mapped via light guides such as 158 and 160 onto the circular regions corresponding to the cross-sectional areas of the upper ends of the light guides 158, 160 etc. and denoted by reference numerals 162 and 164.

Although not shown the light guides may themselves be silvered (as by an aluminium coating), or clad with transparent material of lower refractive index, so as to increase the internal reflectivity of the light guides and prevent light loss through the walls of the light guides.

Figure 8:
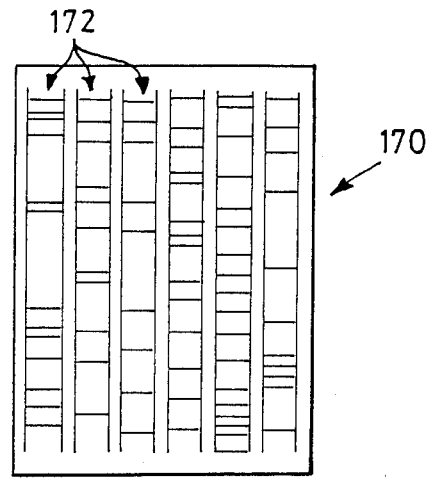
FIGS. 8 and 8A show a modification required for gel electropphoresis.
Figure 8A:
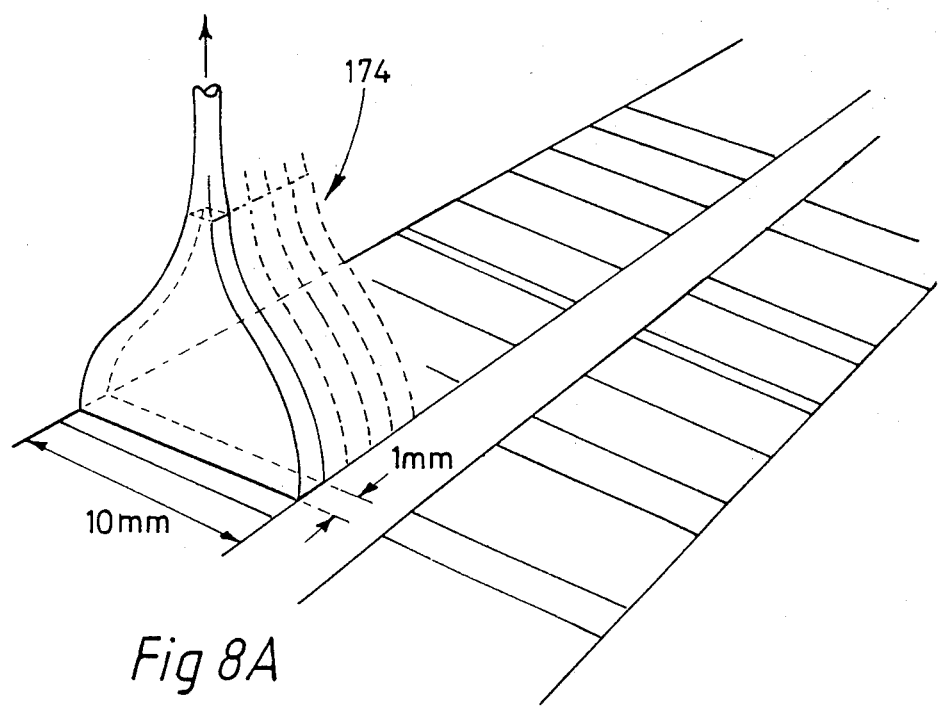

Finally FIGS. 8 and 8A show, as an embodiment of example (c) hereinbefore mention the application of the invention to gel electrophoresis. An electrophoresis sample 170 of dimensions 15 cm by 20 cm carries information in six stripes 172 about 2 cm wide. The stripes 172 constitute line sources detected by means of six columns of two hundred shaped light guides 174, as shown in FIG. 8A. The light guides 174 may be of plastics or glass when a scintillator is incorporated in the sample, or if the sample emission is of X-rays, for example, the shaped rectangular ends of the guides can be made of a suitable scintillating material.

We claim:

1. A high resolution optical imaging apparatus comprising a sample holder for carrying one or more samples, an image intensifier having an input face plate means adapted to be optically coupling the sample holder to the image intensifier so that said intensifier simultaneously receives on distinct regions of its input faceplate photon emission respectively emanating from differing sites on the sample holder, photo-electric detecting means coupled to the output of the image intensifier simultaneously to detect the respective photon emissions, and electronic means coupled to the photo-electric means to produce electrical output signals dependent on the photon emission received at the respective distinct regions of the faceplate, and a signal processing means for relating the respective output signals to the originating sites of photo emission by the sample or samples carried out by the sample holder.

2. Apparatus according to claim 1, in the form of an image quantifier in which the sample holder an undesirable for directly supporting the sample which is made from optic fibre glass, and wherein there is provided an image intensifier having a fibre optic faceplate optically coupled to the underside of the sample holder to receive light, unit area by unit area, from the entire area of the sample, the photoelectric detecting means comprising a CCD sensor having at least one photosite (pixel) for each unit area of the sample, said CCD sensor being optically coupled to the output face of the image intensifier, the electronic means comprising means for cyclically reading the image accumulated on the CCD, and including means drivable by the processed signals output from the processing means to enable an operator to identify any site of interest in the sample.

3. Apparatus according to claim 2, wherein means are provided to control the illumination of the sample whilst viewing by the image intensifier to thereby prevent saturation of the detector.

4. Apparatus according to claim 2, wherein, for viewing self-luminescent samples, all external light sources are excluded.

5. Apparatus according to claim 2, wherein the signal processing means comprises means for digitising the signals obtained from the CCD and means for storing the digitised signals.

6. Apparatus according to claim 5, wherein the stored signals are read out to control a microscope centering device.

7. Apparatus according to claim 6, including a display device driven by the processed signals to display at least part of the sample, thereby to enable sites of interest to be indentified so that the microscope is automatically or manually movable to view a selected site of interest under high power, avoiding a requirement for low power scanning of the entire sample.

8. Apparatus according to claim 2, having a fibre optic coupler coupling the image intensifier to the CCD.

9. Apparatus according to claim 8, wherein the fibre optic coupler is a demagnifying coupler.

10. Apparatus according to claim 2, wherein light from any one unit area of the sample is spread over a small plurality of CCD pixels.

11. Apparatus according to claim 2, wherein the CCD is cooled to improve signal to noise ratio.

12. Apparatus according to claim 2, wherein the image accumulated on the CCD is read out at at least TV frame rates using CCIR standards.

13. Apparatus according to claim 2, wherein the sample holder comprises a fibre optic bottom plate having a shallow well enabling the examination of liquid samples, the sample holder also having an upper glass plate located against the lower plate by means of a positioning ring to ensure efficient contact between the sample and the said lower plate.

14. Apparatus according to claim 13, wherein the two plates are then clamped together and are located for observation by a microscope from above, and detection and measurement by the image quantifier from below.

15. Apparatus according to claim 1, in the form of a photon detector capable of responding to very low rates of photon emission comprising an image intensifier adapted to be positioned so as to receive on discreet regions of its input faceplate photon emission from each of a plurality of reaction sites, a photo electric sensor coupled to the output of the image intensifier to produce an electrical output current as an output signal dependent on the photon emission received at the input of the image intensifier, from each of the reaction sites associated therewith; and circuit means for storing the electrical output currents as separate output signals in a manner which enables the separate output signals to be related to the originating reaction sites, the output signals thereby obtainable from the device corresponding to the photon emission, if any, detected from each of the individual reaction sites.

16. Apparatus according to claim 15, wherein each of the reaction sites is coupled separately to the input faceplate of the image intensifier by light guide means adapted to couple each site with a discreet region of the input faceplate of the image intensifier.

17. Apparatus according to claim 16, wherein the light guides reduce in cross-sectional area as between the input ends associated with the sample holder and the output ends associated with the input faceplate of the image intensifier.

18. Apparatus according to claim 15, wherein the sample holder is a tray containing a plurality of wells each for sample containing.

19. Apparatus according to claim 15, wherein the photoelectric sensor is a CCD device.

20. Apparatus according to claim 15, wherein the image intensifier is a multi-stage demagnifying high gain image intensifier.

21. Apparatus according to claim 15 wherein the said circuit means includes a signal integration means and is adapted to correct for pixel dependent black levels and perform flat field corrections during image readout, the total light coming from a single light source being obtained by summing of the contributions from the pixels in a group of pixels which is or are responsive to the light from the particular site.

22. Apparatus according to claim 15, wherein the said circuit means includes a flash analogue to digital converter producing a digital signal value corresponding to the electrical charge associated with each pixel.

23. Apparatus according to claim 15, wherein the photosensor is a CCD device cooled by Peltier cooling.

24. Apparatus according to claim 21, including computer controlled shutters utilised to mask automatically high flux sites during a long integration cycle.

25. Apparatus according to claim 15, wherein the reaction sites comprise a plurality of columns of line sources of radiation enabling detection in gel electrophoresis.

26. Apparatus according to claim 15, for multiple lumienscent assay measurement, comprising an image intensifier; means for receiving and supporting a tray containing a plurality of regularly arranged reaction wells, so that light emitted from the wells is received by discreet regions of the faceplate of the image intensifier; a multi-element photo electric array detector adapted to receive light from the output of the image intensifier and to produce electrical output signals indicative of the light received from each cell during an integration period; and electrical circuit means for controlling the integration time and producing electrical output signals whose values correspond to the photon emission from the related wells in the tray.

27. A method of operating a microscope and image intensifier combination usable to view a sample carried by a sample holder, the image intensifier having distinct regions of its input faceplate individually coupled to differing sites on the sample holder, according to which positioning of the microscope for high magnification viewing of a site of interest is enabled by low magnification examination of the complete sample holder with the image intensifier.

* * * * *